US012117377B2

(12) United States Patent
Dutta

(10) Patent No.: US 12,117,377 B2
(45) Date of Patent: Oct. 15, 2024

(54) PLATFORM FOR SAMPLING VIRAL PARTICLES ON SURFACES, POROUS STRUCTURES, AND IN THE AIR

(71) Applicant: University of Wyoming, Laramie, WY (US)

(72) Inventor: Debashis Dutta, Laramie, WY (US)

(73) Assignee: UNIVERSITY OF WYOMING, Laramie, WY (US)

( * ) Notice: Subject to any disclaimer, the term of this patent is extended or adjusted under 35 U.S.C. 154(b) by 335 days.

(21) Appl. No.: 17/388,777

(22) Filed: Jul. 29, 2021

(65) Prior Publication Data

US 2022/0034763 A1 Feb. 3, 2022

Related U.S. Application Data

(60) Provisional application No. 63/058,638, filed on Jul. 30, 2020.

(51) Int. Cl.
*G01N 1/22* (2006.01)
*G01N 33/569* (2006.01)
*G01N 1/02* (2006.01)

(52) U.S. Cl.
CPC ......... *G01N 1/2273* (2013.01); *G01N 1/2205* (2013.01); *G01N 33/56983* (2013.01); *G01N 2001/028* (2013.01)

(58) Field of Classification Search
CPC ............... G01N 1/2273; G01N 1/2205; G01N 33/56983; G01N 2001/028; G01N 1/4055; G01N 1/02
See application file for complete search history.

(56) References Cited

U.S. PATENT DOCUMENTS 4,961,916 A * 10/1990 Lesage ................. G01N 1/2205 55/318
2016/0025603 A1* 1/2016 Kindt .................. G01N 1/2205 422/534

FOREIGN PATENT DOCUMENTS

EP 1209223 A1 * 5/2002 ........... G01N 33/569
JP 2000069961 A * 3/2000 ............. A61K 33/42
WO 2016014455 A1 1/2016

OTHER PUBLICATIONS

English Machine Translation of Shiba (JP 2000-69961A), Mar. 7, 2000, translated online Feb. 2024 (Year: 2000).*
Dietz; Leslie et al. Mar. 26, 2021. Exploring Integrated Environmental Viral Surveillance of Indoor Environments: A comparison of surface and bioaerosol environmental sampling in hospital rooms with COVID-19 patients. 28 pages.
(Continued)

*Primary Examiner* — David Z Huang
(74) *Attorney, Agent, or Firm* — Goodhue, Coleman & Owens, P.C.

(57) ABSTRACT

A platform for sampling viral particles on surfaces and porous structures and in the air. The sampling platform includes, for example, a collection pad configured for quantitating viral loads in a fomite or captured form the air. A reservoir or liquid container is associated with the collection pad for interacting a virus collection zone of the collection pad. A liquid medium is disposed within the container. At least one pump is operably configured to move the liquid medium or air through the collection pad for extracting viral particles from the environment.

20 Claims, 8 Drawing Sheets

(56) References Cited

OTHER PUBLICATIONS

Horve; Patrick Finn, Dietz; Leslie, Northcutt; Dale, Stenson; Jason, Wymelenberg; Kevin Van Den. Evalutation of a Bioaerosol Sampler for Indoor Environmental Surveillance of Severe Acute Respiratory Syndrom Coronavirus 2. (2021) 20 pages.

Thermoscientific. A nursing home safeguards their residents with AerosolSense Sampler, an in-air pathogen surveillance solution. Date:N/A. 3 pages.

ThermoScientific. AerosolSense 2900 Sampler Manual. Jun. 10, 2021. 28 pages. https://www.thermofisher.com/order/catalog/product/AEROSOLSENSE?SID=srch-srp-AEROSOLSENSE#/AEROSOLSENSE?SID=srch-srp-AEROSOLSENSE.

Thermoscientific. AerosolSense Sampler, an in-air pathogen surveillance solution: Fast and highly reliable insight into the safety of indoor air. Date: N/A. 2 pages. https://www.thermofisher.com/order/catalog/product/AEROSOLSENSE?SID=srch-srp-AEROSOLSENSE#/AEROSOLSENSE?SID=srch-srp-AEROSOLSENSE.

Thermoscientific. Amidst a pandemic, first responders find confidence and protection with our in-air pathogen surveillance solution. Date:N/A. 3 pages. https://www.thermofisher.com/order/catalog/product/AEROSOLSENSE?SID=srch-srp-AEROSOLSENSE#/AEROSOLSENSE?SID=srch-srp-AEROSOLSENSE.

Thermoscientific. Assessing in-air pathogen transmission indoors. Date:N/A. 1 pages. https://www.thermofisher.com/order/catalog/product/AEROSOLSENSE?SID=srch-srp-AEROSOLSENSE#/AEROSOLSENSE?SID=srch-srp-AEROSOLSENSE.

Thermoscientific. Help protect your organization, community and people in three simple steps. Date:N/A. 1 pages. https://www.thermofisher.com/order/catalog/product/AEROSOLSENSE?SID=srch-srp-AEROSOLSENSE#/AEROSOLSENSE?SID=srch-srp-AEROSOLSENSE.

Thermoscientific. In-air pathogen surveillance solution, AerosolSense Sampler: Frequently asked questions. Date:N/A. 4 pages. https://www.thermofisher.com/order/catalog/product/AEROSOLSENSE?SID=srch-srp-AEROSOLSENSE#/AEROSOLSENSE?SID=srch-srp-AEROSOLSENSE.

Thermoscientific. In-air pathogen surveillance solution: Fast and highly reliable insight into the safety of indoor air. Date:N/A. 6 pages. https://www.thermofisher.com/order/catalog/product/AEROSOLSENSE?SID=srch-srp-AEROSOLSENSE#/AEROSOLSENSE?SID=srch-srp-AEROSOLSENSE.

ThermoScientific. In-air pathogen surveillance solution: Quick start guide. Jun. 25, 2021. 4 pages. https://www.thermofisher.com/order/catalog/product/AEROSOLSENSE?SID=srch-srp-AEROSOLSENSE#/AEROSOLSENSE?SID=srch-srp-AEROSOLSENSE.

Thermoscientific. In-air Pathogens: Proven facts & popular myths. Date:N/A. 1 pages. https://www.thermofisher.com/order/catalog/product/AEROSOLSENSE?SID=srch-srp-AEROSOLSENSE#/AEROSOLSENSE?SID=srch-srp-AEROSOLSENSE.

Wong; Shuk-Ching et al. Airborne transmission of SARS-CoV-2: what is the implication of hospital infection control?. Mar. 18, 2021, 10 pages.

Wong; Shuk-Ching et al. Airborne transmission of severe acute respiratory syndrome coronavirus 2 (SARS-CoV-2): What is the implication of hospital infection control?. Infection Control & Hospital Epidemioloty (2021), 1-2.

\* cited by examiner

PROVIDING A SAMPLING PLATFORM FOR QUANTIFYING A VIRAL LOAD
STEP 200

PLACING THE COLLECTION PAD ON TO A BASE OF THE SAMPLING PLATFORM
STEP 202

PASSING AIR THROUGH THE COLLECTION PAD TO EXTRACT VIRAL PARTICLES FROM AN ENVIRONMENT
STEP 204

REMOVING THE VIRAL COLLECTION ZONE FROM THE COLLECTION PAD
STEP 206

DISSOVLING THE VIRAL COLLECTION ZONE IN THE LIQUID MEDIUM
STEP 208

FIG. 6

```
┌─────────────────────────────────────────────────────┐
│         OBTAIN FOMITE WITH VIRAL LOADING            │
│                     STEP 300                        │
└─────────────────────────────────────────────────────┘
                          │
┌─────────────────────────────────────────────────────┐
│         LOAD RESERVOIR WITH LIQUID MEDIUM           │
│                     STEP 302                        │
└─────────────────────────────────────────────────────┘
                          │
┌─────────────────────────────────────────────────────┐
│  SECURE FOMITE TO COLLECTION PAD OF THE SAMPLING    │
│                     PLATFORM                        │
│                     STEP 304                        │
└─────────────────────────────────────────────────────┘
                          │
┌─────────────────────────────────────────────────────┐
│  MOVE LIQUID MEDIUM FROM THE RESERVOIR THROUGH      │
│         FOMITE WITH PRESSURE OR VACCUM              │
│                     STEP 306                        │
└─────────────────────────────────────────────────────┘
                          │
┌─────────────────────────────────────────────────────┐
│       ENTRAIN VIRAL PARTICLES IN LIQUID MEDIUM      │
│                     STEP 308                        │
└─────────────────────────────────────────────────────┘
                          │
┌─────────────────────────────────────────────────────┐
│         FILTER LIQUID MEDIUM AND VIRAL PARTICLES    │
│                     STEP 310                        │
└─────────────────────────────────────────────────────┘
                          │
┌─────────────────────────────────────────────────────┐
│  COLLECT VIRAL PARTICLES AND LIQUID MEDIUM IN A     │
│                    CONTAINER                        │
│                     STEP 312                        │
└─────────────────────────────────────────────────────┘
```

FIG. 7

```
┌─────────────────────────────────────────────────────────────┐
│   PROVIDING A COLLECTION PAD FOR QUANTIFYING A VIRAL LOAD   │
│                          STEP 400                           │
└─────────────────────────────────────────────────────────────┘
                              │
                              │
┌─────────────────────────────────────────────────────────────┐
│   COLLECTING A VIRAL LOAD FROM AN ENIVORNMENT ON THE COLLECTION │
│                            PAD                              │
│                          STEP 402                           │
└─────────────────────────────────────────────────────────────┘
                              │
                              │
┌─────────────────────────────────────────────────────────────┐
│ DISSOLVING THE COLLECTION PAD IN A LIQUID MEDIUM TO CREATE A LIQUID │
│                          SOLUTION                           │
│                          STEP 404                           │
└─────────────────────────────────────────────────────────────┘
                              │
                              │
┌─────────────────────────────────────────────────────────────┐
│       QUANTITATING THE VIRAL LOAD IN THE LIQUID SOLIUTION   │
│                          STEP 406                           │
└─────────────────────────────────────────────────────────────┘
```

FIG. 8

PLATFORM FOR SAMPLING VIRAL PARTICLES ON SURFACES, POROUS STRUCTURES, AND IN THE AIR

PRIORITY STATEMENT

This application claims priority to U.S. Provisional Patent Application 63/058,638, filed on Jul. 30, 2020, entitled PLATFORM FOR SAMPLING VIRAL PARTICLES ON SURFACES AND POROUS STRUCTURES, hereby incorporated by reference in its entirety.

FIELD OF THE INVENTION

The present disclosure relates to medical diagnostic assays and pathogen detection. More particularly, but not exclusively, the present disclosure relates to a method and platform for sampling viral particles, pathogen detection and running medical diagnostics on surfaces, porous structures and in the air.

BACKGROUND

Several viral respiratory infections (VRI) and pathogens are known to be transmitted through droplets generated during coughing, sneezing, speaking and breathing by symptomatic patients as well as asymptomatic and pre-symptomatic people and animals. As a result, the use of facial coverings is highly recommended, if not required, in all public settings for minimizing community transmission of VRIs and pathogens. Interestingly, while such coverings are useful in preventing the spread of the viruses, biological or chemical reagents from an infected person to other people, they unfortunately may also serve as fomites for transmission of the same virus or biological and chemical reagents to healthy individuals.

Therefore, there is a vital need for quantitating the viral load or pathogen accumulated in various environments and in facial masks/coverings after being exposed to the various environments in order to better understand the level of protection these coverings may offer to healthy subjects or what level of protection may be necessary in a specific environment.

SUMMARY

Therefore, it is a primary object, feature, and/or advantage of the present disclosure to improve on the state of the art and overcome the deficiencies within the art.

It is a further object, feature, or advantage of the present disclosure is to provide a sampling platform for quantitating the viral load accumulated in facial masks and other coverings for providing a simple and non-invasive route to testing for exposure to VRIs, complementing current diagnostic assays performed on nasal/throat swabs and saliva samples among others.

It is a still further object, feature, or advantage of the present disclosure is to provide a sampling platform to meet the vital need for quantitating viral loading for viral particles in the air of various environments by capturing a sample of viral particles.

Another object, feature, or advantage is to provide a sampling platform that is inexpensive, disposable and operable by untrained individuals which could allow their wide use for diagnostic applications as well as for assessment of viral transmission through the concerned porous structures and surfaces and in the air.

Another object, feature, or advantage is to provide a water-soluble fabric that collects viral particles, biological reagents, or chemical reagents in aerosols or deposited on solid surfaces.

Yet another object, feature, or advantage is to provide a sampling platform that when operated ensures minimal exposure of the user to the viral particles, biological reagents and chemical reagents trapped in the clothing/porous structure and floating in the air.

In an aspect of the present disclosure, a platform for sampling viral particles on surfaces and porous structures is disclosed. The sampling platform includes, for example, a working surface configured for quantitating viral loads in a fomite. A reservoir is associated with the working surface for interacting with the fomite. A liquid medium is disposed within the reservoir. At least one pump is operably configured to move the liquid medium through the fomite for extracting viral particles from the fomite. At least one container is operably connected to the pump for collecting the viral particles.

In another aspect of the present disclosure, A platform for sampling viral particles in an environment and on surfaces is disclosed. The sampling platform includes, for example, a collection pad configured for quantifying vial loads in an environmental sample, the collection pad comprising a virus collection zone and an impervious zone, and a base operably connected to the collection pad, the base comprising a housing. At least one pump is operably configured to move air through the collection pad for extracting viral particles from the environmental sample, the at least one pump disposed within the housing. A container configured to collect the viral particles and a liquid medium is disposed within the at least one container, the solvent configured to dissolve at least the virus collection zone.

In another aspect of the present disclosure a collection pad for sampling viral particles is disclosed. The collection pad includes, for example, an impervious zone comprised of material impervious to viral particles. A viral collection zone is configured capture viral particles from an environmental sample, wherein the viral collection zone comprises a plurality of pores and water-soluble fabric. A mesh support structure, the mesh support structure connected to the viral collection zone and the impervious zone.

In another aspect of the present disclosure, a method for sampling viral particles on surfaces and porous structures is disclosed. The method includes, for example, in at least one aspect, the steps of providing a working surface configured for quantitating viral loads in a fomite, a reservoir associated with the working surface for interacting with the fomite, and an liquid medium 106 disposed within the reservoir, placing the fomite on the working surface, passing the liquid medium 106 through the fomite for extracting the viral particles with the liquid medium 106, and collecting the viral particles and liquid medium in a container.

In another aspect of the present disclosure a method for quantifying a viral load from an environmental sample is disclosed. The method includes for examples, in at least one aspect, the steps of providing a sampling platform configured for quantifying viral loads in an environment, the sampling platform comprising a collection pad and a base, placing the collection pad on the base, passing air through the collection pad for extracting the viral particles from the environmental sample, removing a viral collection zone from the collection pad, and dissolving the viral collection zone in a solvent disposed within a container to form a resulting solution.

One or more of these and/or other objects, features, or advantages of the present disclosure will become apparent from the specification and claims that follow. No single embodiment need provide each and every object, feature, or advantage. Different embodiments may have different objects, features, or advantages. Therefore, the present disclosure is not to be limited to or by any objects, features, or advantages stated herein.

BRIEF DESCRIPTION OF THE DRAWINGS

Illustrated embodiments of the disclosure are described in detail below with reference to the attached drawing figures, which are incorporated by reference herein, and where:

FIG. 6 is a flowchart for quantitating viral loading with the sampling platform in accordance with an exemplary aspect of the present disclosure;

FIG. 7 is another flowchart for quantitating viral loading with the sampling platform in accordance with an exemplary aspect of the present disclosure; and FIG. 8 is another flowchart for quantitating viral loading, biological reagents or chemical reagents with a water-soluble fabric in accordance with an exemplary aspect of the present disclosure.

DETAILED DESCRIPTION

Figure 1:
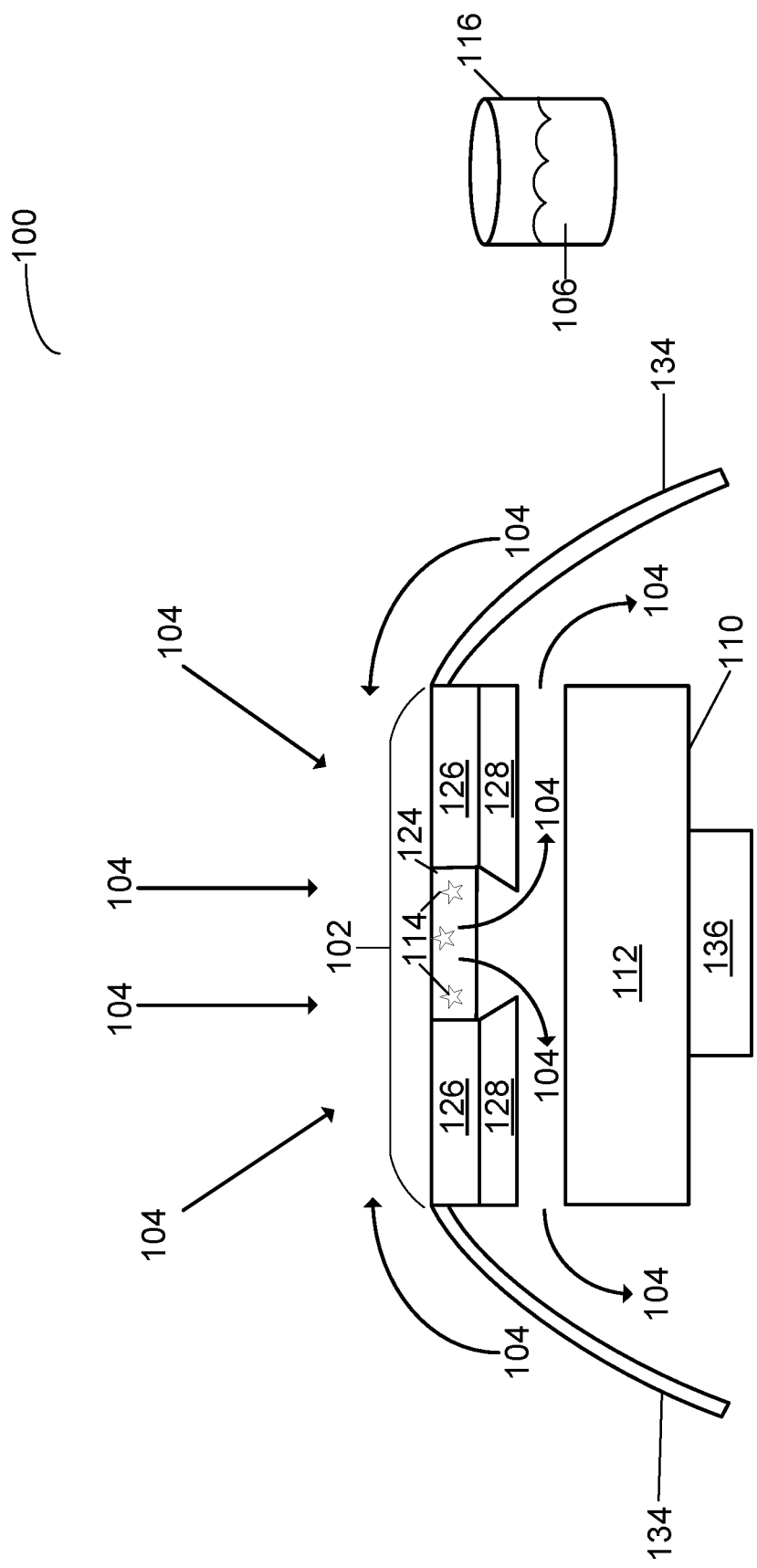
FIG. 1 is an illustration of one aspect of the sampling platform for sampling viral particles trapped in clothing, other porous structures and in the air.
Figure 2:
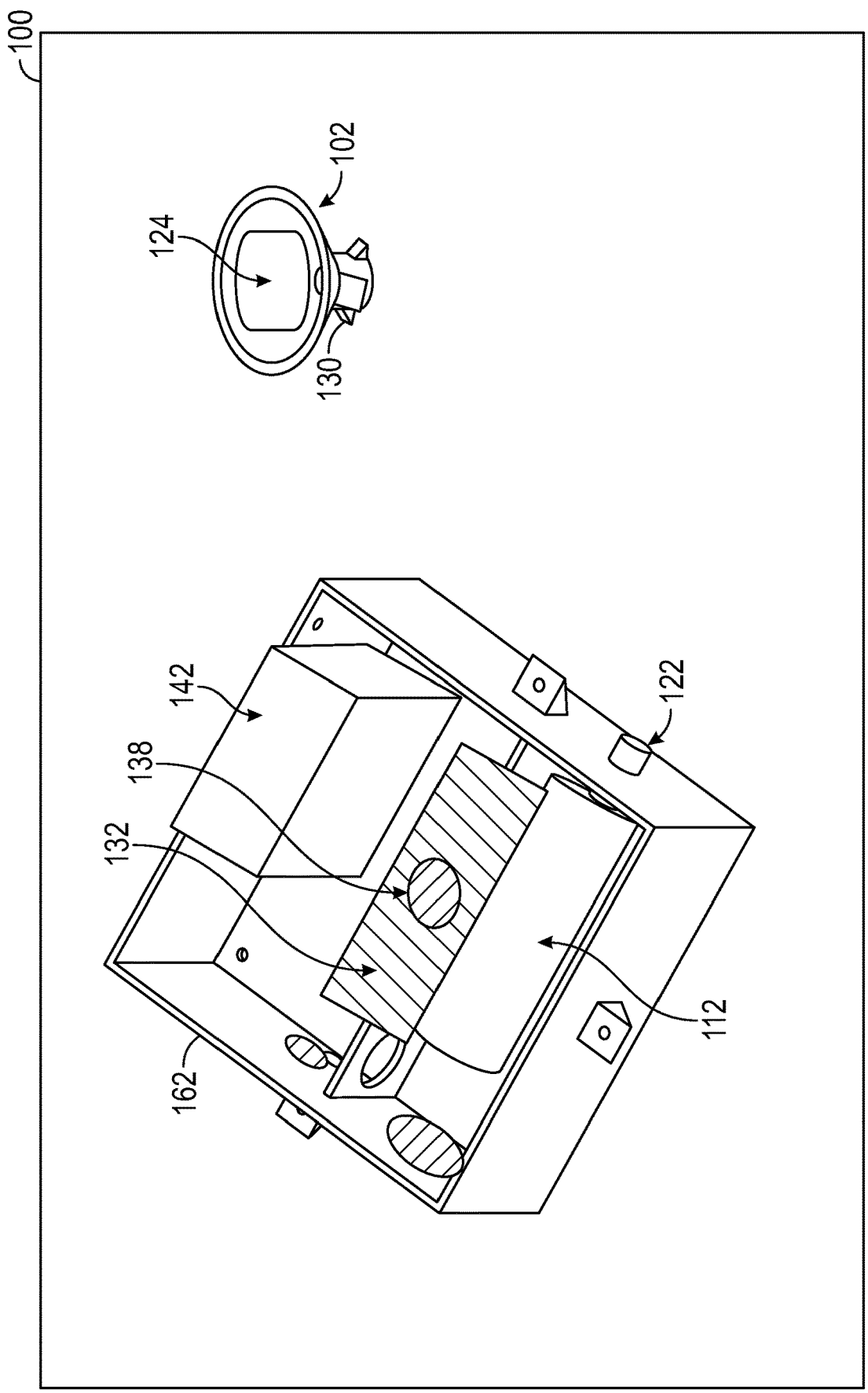
FIG. 2 is an illustration of another aspect of the sampling platform for sampling viral particles trapped in clothing, other porous structures and in the air.
Figure 3:
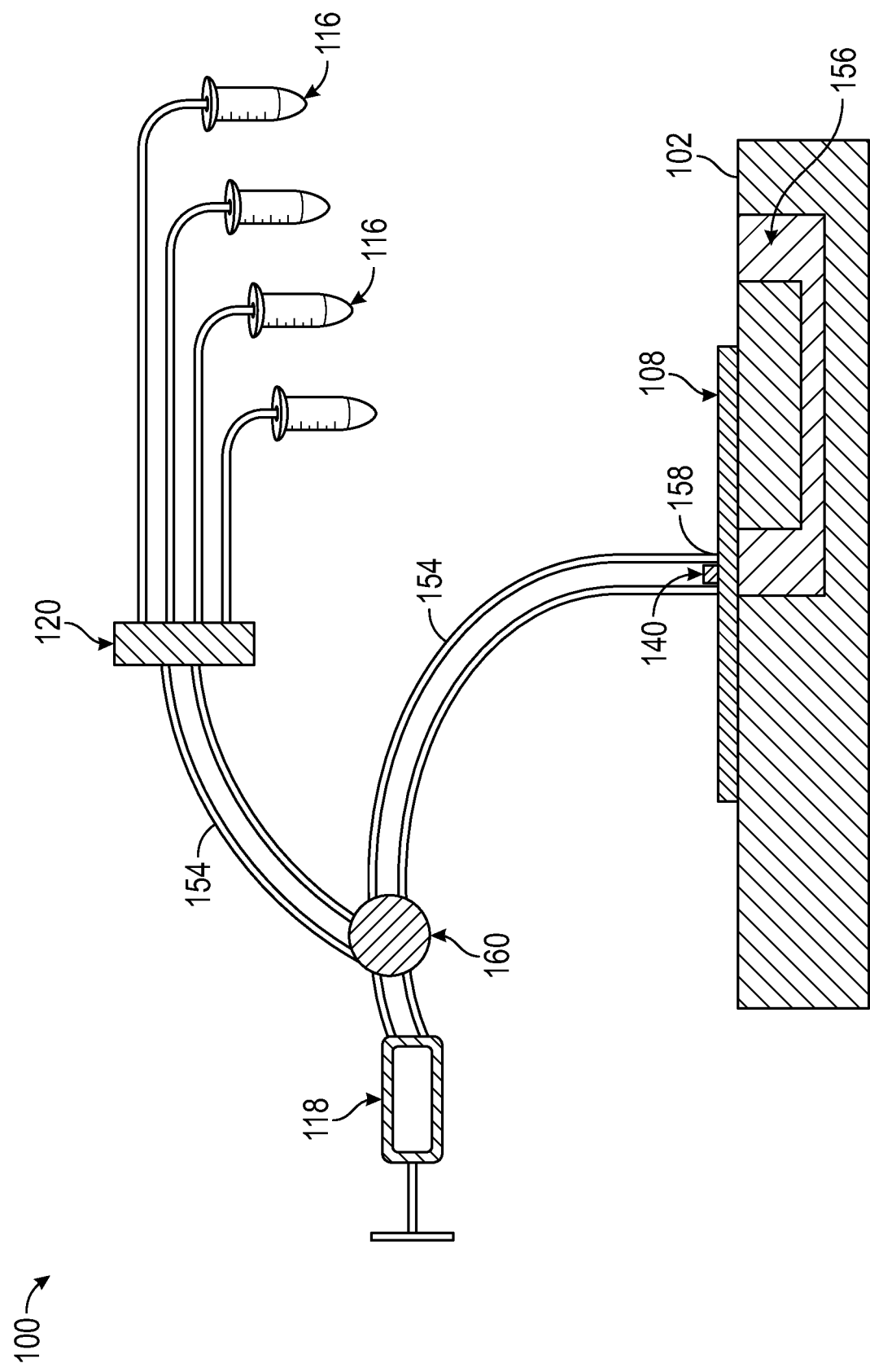
FIG. 3 is an illustration of another aspect of the sampling platform for sampling viral particles trapped in clothing, other porous structures and in the air.
Figure 4:
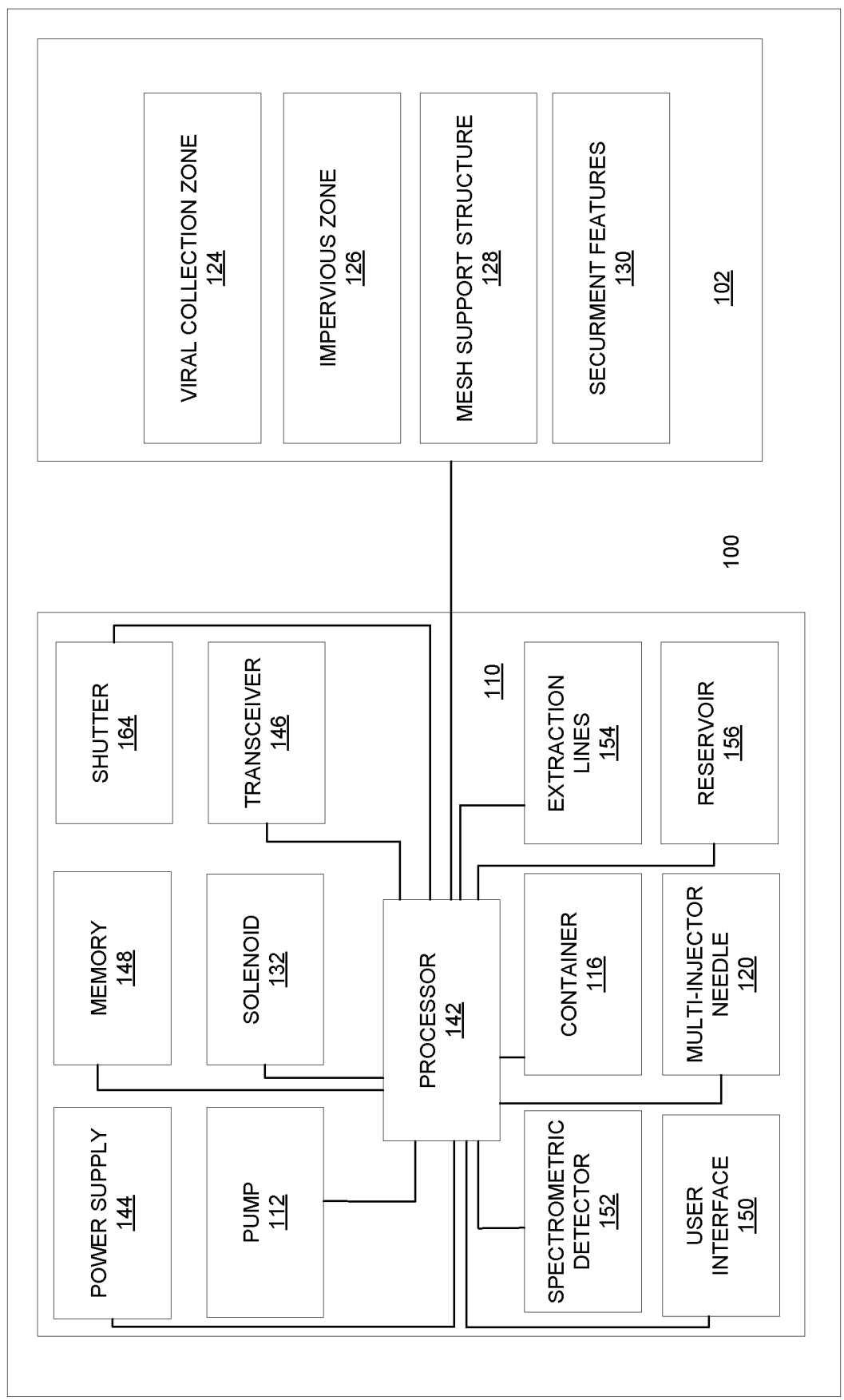
FIG. 4 is an illustration of another aspect of the sampling platform for sampling viral particles trapped in clothing, other porous structures and in the air.

The present disclosure is related to quantifying viral loads in various environments and a platform for sampling viral particles on surfaces, porous structures and in the air. Viral particles and viral loads including more generally any biological or chemical reagents. Representative applications of methods and systems are described in this section. These examples are being provided solely to add context and aid in the understanding of the described aspects of the disclosure. It will thus be apparent to one skilled in the art that the described aspects of the disclosure may be practiced without some and/or all of these specific details. In other instances, well known process steps have not been described in detail in order to avoid unnecessarily obscuring the described embodiments. Other applications are possible, such that the following examples should not be taken as limiting.

In the following detailed description, references are made to the accompanying drawings, which form a part of the description and show, by way of illustration, specific embodiments in accordance with the methods and systems of the present disclosure. Although aspects of the disclosure are described in sufficient detail to enable one skilled in the art to practice the described embodiments, it is understood that these examples are not limiting; other aspects may be used, and changes may be made without departing from the spirit and scope of the described aspects of the disclosure.

It has been estimated that people spend about 90% of their time in both private and public indoor and outdoor environments, such as homes, gyms, schools, workplaces, transportation vehicles, etc. Thus, indoor air quality has a significant impact on our health and well-being in general. For many people, the health risks from exposure to indoor air pollution may be greater than those related to outdoor pollution. In particular, poor indoor air quality can be harmful to vulnerable groups such as children, young adults, the elderly, or those suffering chronic respiratory and/or cardiovascular diseases.

Among other contaminants, the presence of airborne pathogens adversely affects the indoor air quality. Several VRI are known to be transmitted through droplets generated during coughing, sneezing, speaking, and breathing by symptomatic patients as well as asymptomatic and pre-symptomatic people. Unfortunately, humans and animals infected with such pathogens can serve as sources for these infectious agents constantly introducing them into our environment. For example, several respiratory viruses including the causal agents for COVID-19 and influenza A, i.e., the SARS-CoV-2 and H1N1 viruses, respectively, are known to be transmitted through aerosols and droplets generated during coughing, sneezing, talking, and breathing by symptomatic, asymptomatic, and pre-symptomatic individuals. The current COVID-19 pandemic has shown us the extent of damage an emerging respiratory virus can bring about to human lives and global economies over the period in which vaccines and medical treatments are developed against it. Unfortunately, even upon availability of a vaccine and treatment, common flu is estimated to cause about 290,000-650,000 human deaths worldwide each year. As a result, regular and reliable inspection of our local environment for the presence of respiratory viruses is a topic of high significance to our society and is likely to receive a lot of attention in the post COVID-19 pandemic period and beyond. Periodic monitoring for respiratory viruses in indoor and outdoor air by capturing viral particles in aerosols or deposited on surfaces not only can minimize airborne transmission of these pathogens but also allow individuals exposed to them seek medical attention in a timely manner.

As a result, the use of facial coverings is highly recommended, if not required, in all public settings for minimizing community transmission of VRIs. Interestingly, while such coverings are useful in preventing the spread of the virus from an infected person to other people, they unfortunately may also serve as fomites for transmission of the same virus to healthy individuals. In this scenario, there is a vital need for quantitating the viral load accumulated in facial masks and other coverings after being exposed to various environments in order to better understand the level of protection these coverings may offer to healthy subjects. Moreover, such quantitation also presents a simple and non-invasive route to testing for exposure to VRIs, complementing current diagnostic assays performed on nasal/throat swabs, saliva samples, and the like. Such assays remain critical for monitoring the spread of VRIs across different communities besides allowing the identification and isolation of individuals who may serve as carriers for the virus.

Several types of airborne virus-collection systems exist in the market today. These include impactors, cyclones, filters, impingers, electrostatic precipitators and water-based growth tube collectors. While impactors rely on particles in the incoming airstream to accelerate through small nozzles (holes/slits), and those with high inertia to impact onto the surface of collection media, the cyclones use centrifugal forces to deviate particles from the airflow to impact onto the collection wall. Impingers on the other hand, exploit the abrupt change in the airstream direction inside the bottle to impact particles into the liquid collection medium whereas in filtration devices, particles are collected onto filter media through interception, inertial impaction, and diffusion. Electrostatic precipitators, however, work on a different principle, where particles are first electrically charged through corona discharge to create electrostatic attraction that draws the charged particles to oppositely charged collection plates. And finally, in water-based growth tube collectors, cold aerosol particles are introduced into a warm growth tube saturated with water vapor which allows encapsulation of small particles into larger droplets, thus enabling efficient collection of these enlarged particles through gentle impaction. Once captured onto a collection surface/media, the virus can be then detected using a variety of techniques ranging from traditional animal models, virus isolation in cell cultures to nucleic acid-based technologies such as PCR, quantitative PCR and RT-PCR, and biochemical tests such as ELISA. It must be pointed out, however, that the procedures followed to transfer the virus material into a liquid medium (as is needed for a majority of the platforms noted above) involve several manual sample handling steps rendering the process slow and expensive as well as compromising its reproducibility.

As evident from these descriptions, currently available platforms/procedures for quantitating airborne viruses tend to be bulky/labor-intensive, noisy, energy-intensive and expensive, and often expose the individual performing the procedures to the pathogen. Moreover, these systems typically require special skills to operate as well as maintain and cannot be integrated to buildings or transportation vehicles without significantly modifying their framework. Interestingly, a portable virus-collection unit similar to that proposed in this project was recently reported in the literature. However, the noted unit relies on detecting airborne viruses based on an immunoassay performed using polystyrene beads. While the integration of the virus-collection and detection modules on the reported platform offers several advantages over the commercially available airborne virus-collection systems, including portability and rapid detection of the pathogens, it also has some distinct limitations. Recent reports show that the detection limit for SARS-CoV-2 is a billion-fold lower using the RT-PCR method compared to that realized employing immunoassays (0.1 copy/μL versus 108 copy/μL). Moreover, integrating the device does not allow one to perform multiplex assays on the sample as well as easily adapt the technology to different pathogens and other air pollutants. Furthermore, an integrated virus-collection and detection platform is inherently complicated subjecting the overall process to more-frequent failures, as well as increasing the price for testing an air sample.

A simple and cost-effective approach to monitoring for respiratory viruses in indoor air is disclosed. The inexpensive and portable nature of our unit will allow its deployment in enclosed spaces ranging from small households and offices to large facilities such as warehouses, hospitals, airports, private residences, commercial and government building operators, clinics, elder care facilities, schools, hotels, barns, meat packing plants, transportation vehicles as well as regional medical laboratories without having to modify the building infrastructure. In addition, these units may be easily installed in, for example, planes, trains, buses and taxis in a cost-effective manner. The size of the region or environment from which the sampling platform would be collecting air samples or aerosols will mostly depend on the air-pump ratings as well as other factors like shape/size of the room, airflow in it, and air disturbances. Multiple sampling platforms may need to be deployed in large rooms. The plurality of sampling platforms may need to be spaced apart at specific distances in order to sample the entire environment or to disinfect the entire environment.

The current disclosure addresses the noted need through development of a sampling platform 100 for viral particles trapped in clothing including common facial masks, air filters, clothing, medical gloves, and other coverings and other porous structures after being exposed to various environments. This sampling platform 100 comprises a base plate 110 with a reservoir 156 for holding the sample liquid medium 106, such as the exemplary sampling platform 100 shown in FIGS. 1-4. In at least one aspect, the liquid medium 106 can be a Viral Transport Medium (VTM) as recommended by the Center of Disease Control or a commercially available reagent such as the Universal Viral Transport System marketed by Becton, Dickinson and Company. The sampling platform may be easily coupled to established systems such as RT-qPCR units, immune assay units, electrochemical units or other sensing and detection units, for quantitating viral load in the extracted samples, minimizing exposure of its users to the viral particles during the process.

The sampling platform 100 apparatus, system and method for quantifying viral loads addresses these limitations of current airborne pathogen monitoring systems by developing a sampling platform 100 that will be smaller, such as a platform that fits within a human palm and lighter, such as less than 100 grams, than a typical cell phone and will work drawing power, such as less than 200 mW of power, as shown in FIGS. 1-4. A collection pad 102 attached to this unit will continuously collect aerosols/droplets from its local environment over a period of a few hours to several days by drawing ambient air 104 through it using a vacuum pump 112. The collection pad 102 will involve a porous region for airflow that will be made out of polyvinyl alcohol (PVA), a water-soluble material. The water solubility of PVA will allow dissolution of the virus-collection zone 124 in an aqueous buffer or liquid medium 106 allowing easy extraction of the RNA, DNA, protein, lipids or chemical reagent markers that can then be analyzed using the RT-PCR, RT-LAMP, immunoassays, electrochemical methods or other sensing techniques to determine the amount of captured virus particles 114.

In one aspect of the present disclosure, the extraction process can be initiated by flushing the liquid medium 106 through the porous clothing or fomite 108, collection pad 102 or other structure housing the viral particles in a controlled manner after mechanically securing it to the base plate 110. The flow of the liquid medium 106 through the clothing 108, collection pad 102, or other porous structure can be induced using a syringe pump 112 by pulling its plunger by a chosen distance manually or with a syringe pump 112 or other type of mechanical, pneumatic or electrical pump 112. After having extracted the virus sample 114 into a tubing 154 and/or the syringe barrel 118, it can then be aliquoted into containers 116 by returning the syringe plunger back to its original position. A multi-injector needle 120 can be used to create multiple aliquots of the virus sample 114 for each of the extraction procedures. The sampling platform 100 is inexpensive and disposable and can be designed for use in field settings by individuals with limited scientific expertise. In addition, the sampling platform 100 may be operated ensuring minimal exposure of the user to the viral particles 114 trapped in the clothing or other porous structures or in the air. The sampling platform 100 of the present disclosure may also be employed for quantitating viral loads 114 on various surfaces or in the air. In this application, the concerned surface can be wiped using a piece of cloth 108 or other (sample collecting) material(s), which then is sampled for its viral load using the sampling platform shown, for example, in FIGS. 1-4.

In another aspect of the present disclosure, the extraction process can be initiated by air being continuously captured by the sampling platform 100. The air may be captured using a portable vacuum pump 112 or an air pump 112. The air 104 flows through a collection pad 102 which captures viral particles 114. The collection pad 102 may be detachable allowing the collection pad 102 to be replaced if necessary. In some aspects, the collection pad may swab a surface to collect viral particles deposited on the surface prior to being placed or connected to the base 110 of the sampling platform. After air 104 travels through the collection pad 102, the air 104 may exit the sampling platform 100 using one or more air exits 122. The collection pad 102 can be removed and placed in a liquid container 116 where a virus collection zone 124 of the collection pad 102 is solubilized in a liquid medium 106 with the captured viral particles 114. A RT-PCR or any other analysis can be run on the liquid medium 106 to quantify the viral load 114. The sampling platform 100 can be designed for use in field settings by individuals with limited scientific expertise. In addition, the sampling platform 100 may be operated ensuring minimal exposure of the user to the viral particles 114 trapped in the clothing 108, collection pad 102, or other porous structures. The sampling platform 100 of the present disclosure may also be employed for quantitating viral loads on various surfaces. In this application, the concerned surface can be wiped using a piece of cloth or other (sample collecting) material(s), which then is sampled for its viral load using the sampling platform shown, for example, in FIGS. 1-4.

In at least one aspect of the present disclosure, the sampling platform 100 enables sampling of surfaces, air samples, and porous structures allowing quantitation of their viral loads 114 after being exposed to various environments. The sampling platform 100 is inexpensive, disposable and operable by untrained individuals which allows for wide usage and implementation for diagnostic applications as well as for assessment of viral transmission through the concerned porous structures and surfaces. The sampling platform 100 can also be integrated and integrable to most downstream analysis systems that may quantitate the viral load 114 in the extracted sample.

The sampling platform 100 may run continuously with the collection pad 102 being analyzed a set number of times a week or in a day. The sampling platform 100 may also be run at set times during a day. For example, the sampling platform 100 may run for 10 minutes every hour and the collection pad 102 is analyzed two to three times a week. The analysis and run times may depend on the environment the sampling platform 100 is placed in. In a high traffic environment, such as a hospital waiting room or a transportation waiting area, the collection pad 102 may need to be analyzed every day and the sampling platform 100 may need to be run continuously.

Although procedures for sampling pathogens from porous and non-porous objects and air samples have been reported in the literature, they have poor reproducibility, are labor-intensive, and tend to expose the individual performing the procedures to the pathogen. Currently, pathogen extraction from fomites and other objects are often initiated by wetting a cotton or polyester-tipped swab in an eluent, such as phosphate-buffered-saline, followed by swabbing a few square centimeters of its surface using a firm sweeping and rotating motion. The swab is then placed back into the remaining eluent and vortexed for a few seconds to extract the pathogens into a liquid medium for subsequent analysis. Although this procedure is suitable for sampling pathogenic species from the surface of an object, it is not effective in extracting viral particles trapped within a porous substance. Similarly, the current procedures for sampling pathogens from filters used in air-handling systems involve several manual steps that can compromise the accuracy of the test results. Specifically, these tests rely on manually cutting out pieces of the air filter and immersing them in an appropriate liquid medium to extract the viral particles. While this approach allows better extraction of pathogens trapped within a porous material, it is not time-efficient and can introduce several sources of variability in the test results. Moreover, the extraction procedures described above are challenging to automate and can potentially expose individuals in the test facility to the pathogen. Furthermore, they also make frequent sampling of airborne pathogens an expensive process that requires skilled personnel to complete its different steps.

Figure 5:
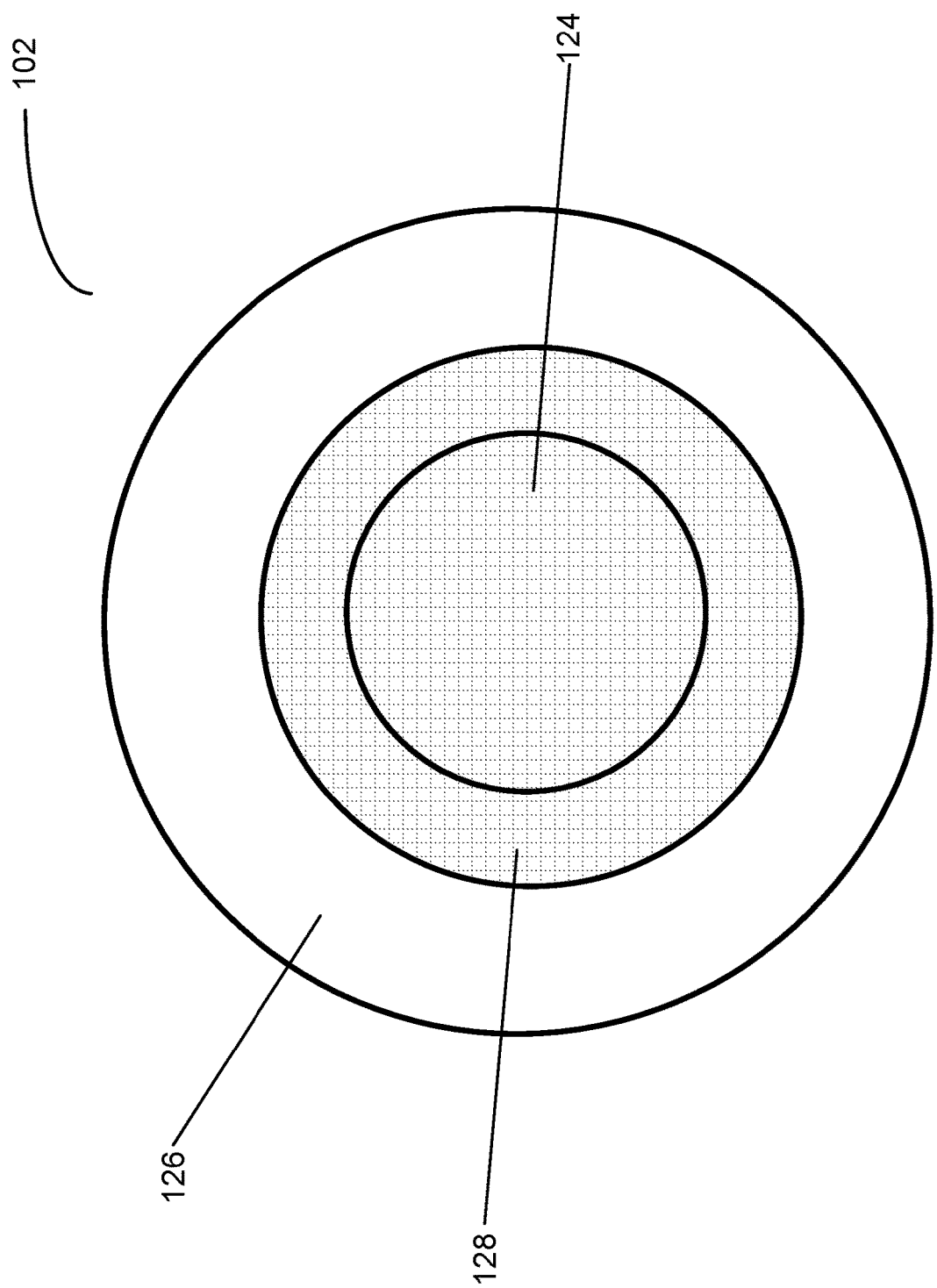
FIG. 5 is an illustration of one aspect of the collection pad for collecting viral particles.

In one aspect of the present disclosure, the sampling platform 100 employs water-soluble pads as collection pads 102 for capturing viruses which is conducive to reliable extraction of the pathogens into a liquid medium 106 and to automation of the major procedures involved. The collection pads 102 have a virus collection zone 124 and an impervious zone 126, as shown in FIG. 5. The virus collection zone is configured to capture viral particles, biological reagents or chemical reagents on water soluble fabric. The collection pad 102 may include water-soluble fibers, such as PVA fibers for capturing airborne viruses. The virus collection zone 124 can be produced using relatively inexpensive water-soluble fabrics, making frequent testing of indoor air an affordable process. A detectable amount RNA, DNA, proteins, lipid samples or chemical reagent markers can be captured on collection pad 102 weighing about 100 mg upon drawing ambient air through them that is contaminated with virus containing aerosols/droplets emitted by an infected individual while breathing and speaking in the vicinity of the pad for 15 minutes. The virus collection zone 124 may include ATP-based polymers or butanediol vinyl alcohol filaments, filaments composed of a blend of a water-soluble polymer (similar to the previous ones) and a sugar, generally trehalose, a polysaccharide that is rapidly soluble in water and with high thermal stability. The collection pad 102 may contain fibers that are insoluble in cold water. The collection pad 102 can be dissolved in warm water to extract the RNA, DNA, proteins, lipid samples or chemical reagent markers into a liquid medium 106, and then cool the resulting liquid slowly to precipitate out the collection pad 102 from the sample. This allows the method to substantially mitigate any adverse effects of PVA on the analytical performance of the PCR/LAMP assays without having to use virus-collection zones 124 that are much smaller than 10 $cm^2$ in size. The size of the virus collection zone 124 may be determined by the amount of the virus collection zone 124 that can be dissolved in the liquid medium 106. The water-soluble fabric may be used to collect any biological or chemical reagent in aerosols or deposited on a surface. The collection pad 102 may be used in medical diagnostic assay to capture DNA, protein and lipid samples emitted by humans or animals breathing, speaking, coughing or sneezing. The collection pad 102 may also be used to collect forensic samples including DNA, RNA, pathogens, protein and lipid samples by swabbing a surface with the collection pad 102 or the viral collection zone 124 and placing the collection pad 102 on the base 110. The collection pad may also collect forensic samples by drawing the forensic sample in through the use of the vacuum trapping the forensic sample on the collection pad 102.

The impervious zone 126 can be comprised of a sheet, cloth, filament or material that is impervious to air or viral particles. The impervious zone 126 may be comprised of a polyvinyl chloride (PVC) sheet. A mesh support structure 128 may be placed, glued or secured underneath the impervious zone 126 to support the collection pad 102, as shown in FIG. 5. The mesh support structure 128 may also be underneath the virus collection zone 124. In one aspect of the present disclosure, a nylon net will be glued on the bottom surface of the PVC sheet to mechanically support a mesh of compacted PVA fibers in the hollow region to create the virus-collection zone 124. The impervious zone 126 may surround the virus collection zone 124. A shape or pattern may be cut out from the impervious zone 126 to surround one or more virus collection zones 124. In one aspect of the present disclosure the impervious zone 126 may have a circular pattern cut out in the center of the impervious zone 126. The virus collection zone 124 is placed in the central hole. The hole in the impervious zone 126 may be cut out with a leather cutting tool, knife, a scissors or any other tool capable of cutting through the impervious zone 126. One or more securement features 130 for mechanically securing a fomite 108 to the collection pad 102 or securing the collection pad 102 to the base of the sampling platform 100. The collection pad 102 materials may be 3D printed using polylactic acid.

The pore volume and airflow resistance of the virus collection zone 124 will be controlled based on the density of the water-soluble fibers as well as the diameter and thickness of the mesh support structure 128. The choice for these parameters can be arrived at based on COMSOL simulations of aerosol flow through the virus collection zone 124. A pump 112 may draw air volumes on through the virus collection zone 124 with pressure drops. Air volumes can range from the order of 1-10 L/min and the pressure drops may be in the range of 100-1000 Pa to allow operation of the sampling platform 100. The pump 112 may be configured to extract the viral particles 114 carried by the liquid medium 106 and actuated to provide a pressure for inserting the viral particles 114 carried by the liquid medium 106 into the reservoir 156 or container 116. The pump 112 may also be comprised of a syringe pump, a mechanical pump, hydraulic pumps, air pump, electric pump or an electrical field may be used to draw air 104 into the sampling platform 100 and trap viral particles 114. A solenoid 132, such as a push-pull solenoid for actuating a shutter 164 or shutter 164 mechanism may be operable connected to the air pump 112 to move the air pump 112. The solenoid 132 moves the shutter 164 from an open position to a closed position allowing the shutter 164 to hold either the open position or the closed position without power being applied. The shutter 164 is configured to prevent the collection pad 102 from collecting debris and dust when the sampling platform 100 is not running. During the period where the sampling platform 100 is programmed to collect viral loads, the shutter 164 will open and allow air 104 to flow through the collection pad 102.

Additionally, the airflow 104 around the sampling platform 100 may directed by air-deflectors 134 to enhance or optimize the aerosol capture in the virus-collection zone 124. The air-deflectors 134 can also enhance or maximize the distance over which air is collected. The air-deflectors 134 can direct air from the sides of the sampling platform 100 on to the collection pad 102. The air deflectors 134 may also prevent wind from moving the sampling platform 100 from a surface holding the sampling platform 100 or from removing the sampling platform 100 from a lift stand 136 holding up the sampling platform 100 or to prevent debris from getting on or into the collection pad 102. The air deflectors 134 may also be used to block or prevent sunlight from interfering with the effectiveness of the sampling platform 100. Suitable shape and size for the air deflectors 134 may be established based on airflow simulations performed using the numerical package COMSOL. An artificial breathing simulator system may be used to then contaminate the air around this platform simulating the emission of virus containing aerosols/droplets by an infected individual while breathing and speaking in its vicinity. The viral particles 114 captured on the collection pad 102 may be subsequently quantified using the RT-PCR, RT-LAMP, immunoassay, electrochemical methods and other sensing techniques. A detectable amount of viral RNA can be captured on the collection pad by drawing the contaminated air at a rate of <10 L/min for 15 minutes upon analysis using the RT-PCR and RT-LAMP methods.

The sampling platform 100 may have a slot 138 or hole for inserting the collection pad 102. This allows the collection pad 102 to be removeable and replaced. The slot 138 may be comprised of a slit, a hole, or any other mechanism for securing the collection pad 102 to a housing 162 of the base 110 of the sampling platform 100. The slot 138 may be located on the shutter 164. A filter 140 may be placed or secured on top of the collection pad 102 to prevent debris from the environment from attaching to or getting caught in the collection pad 102. The filter may include HEPA filters, UV filters, electrostatic filters, washable filters, media filters, spun glass filters, pleated filters, paper filter, or any other type of filter 140 that is configured to filter out debris. The type of filter 140 may be based on the environment the sampling platform is placed in. The sampling platform may have a door allowing a user access to remove the container 116 or to allow the user access to the inside of the sampling platform 100. The housing 162 may house all the components of the base 110 or of the base 110 and the collection pad 102.

The base 110 of the sampling platform may include a processor 142 and power supply 144 for operating the sampling platform 100. The processor 142 controls the operation and functionality of the sampling platform. The processor 142 may be comprised of a circuitry, such as a printed circuit board, chips, one or more microprocessors, digital signal processors, application-specific integrated circuits (ASIC), central processing units, or other devices suitable for controlling the sampling platform. The processor 142 may also process user input to determine commands implemented by the sampling platform 100 or sent to the sampling platform 100 from a remote device through the transceiver 146. The processor 142 is operably connected the pump 112, solenoid 132, shutter 164, air deflectors 134, and other components of the sampling platform 100. The processor 142 may also include programs, scripts, and instructions that may be implemented to operate the sampling platform. The components of the sampling platform 100 may be electrically connected utilizing any number of wires, contact points, leads, busses, wireless interfaces, or so forth.

The power supply 144 may represent a battery, fuel cell, thermal electric generator, AC/DC power, piezo electric charger, solar charger, ultra-capacitor, hybrid storage device, or other existing or developing power storage technologies. The power supply 144 is operably connected to the processor 142. The sampling platform may also include a memory 148. The memory 148 is a hardware element, device, or recording media configured to store data for subsequent retrieval or access at a later time. The memory 148 may be static or dynamic memory. In one embodiment, the memory 148 and the processor 142 may be integrated. The memory 148 may use any type of volatile or non-volatile storage techniques and mediums. The memory 148 may store information related to the status of the sampling platform 100, the length of time the sampling platform 100 was turned on, user settings, a history of the operation of the sampling platform 100 and so forth.

The sampling platform 100 may also include a transceiver 146 operably connected to the processor 142 comprising both a transmitter and receiver which may be combined and share common circuitry on a single housing. The transceiver 146 may communicate utilizing Bluetooth, Wi-Fi, ZigBee, Ant+, near field communications, wireless USB, infrared, mobile body area networks, ultra-wideband communications, cellular (e.g., 3G, 4G, 5G, PCS, GSM, etc.) or other suitable radio frequency standards, networks, protocols, or communications. The transceiver 146 is configured to received user input or commands from a remote device for controlling the sampling platform 100, such as a command to turn the sampling platform on or off.

The sampling platform 100 may have a user interface 150 operably connect to the processor 142, allowing a user to interact with the sampling platform 100. The user interface 150 may be a display screen where a user can provide user input or the user interface 150 may include switches, buttons or any other mechanism allowing the user to interact with the sampling platform 100. The user interface 150 may display an alert that viral particles are being detected, the amount or type of viral particles or whether the air has been disinfected.

A spectrometric detector 152, such as a front-end spectrometric detector, that would sense an increase in aerosol concentration around the sampling platform 100 may be operably connected to the processor 142. The spectrometric detector 152 may trigger the sample collection process if the aerosol or viral quantity detected surpasses a threshold. The user may set the threshold using the user interface 150 or from a remote device. The readings of the spectrometric detector 152 may be visible on the user interface 150. Once the aerosol concentration drops below a certain threshold, the sampling would stop. The collection pad 102 may be analyzed each time the spectrometer detector 152 is triggered.

A plurality of extractions lines 154 may be operably connected to the pump connecting the viral collection pad 102 to a collection reservoir 156. The extraction line 154 may aid in directing air 104 from the collection pad 102 through the sampling platform 100 towards one or more exits 122. In other aspects the extraction line 154 may be operably connected to the vacuum pump 112, collection pad 102, and liquid medium container 116. The extraction line 154 may aid in directing viral particles 114 or filaments of the virus collection zones 124 that have broken off into the liquid medium container 116. The extraction line 154 may have a filter 140 for filtering a liquid medium 106 extracted from the fomite 108 secured to the collection pad 102 or the collection pad 102 itself at an inlet side 158 of the extraction line 154. A multiway valve 160, such as a three way stop valve, is operably connected to the extraction line 154 and to the pump 112. The multiway valve 160 may be located proximate to the collection pad 102 or the liquid medium container 116. The multiway valve 160 may aid in the transfer of the viral particles 114 from the collection pad 102 through the extraction line 154 and into the liquid medium container 116. It may seal the liquid medium container 116 from the collection pad 102 when the sampling platform 100 is not collecting viral particles 114 or when the sampling platform 100 is done collecting viral particles 114. At the end of the extraction line 154 there may be a multi-injector needle 120 for injecting the collection pad 102, viral particles 114, or liquid medium 106 containing the collection and viral particles into the container 116. The shutter 164 may be operably connected to the plurality of extraction lines 154.

The sampling platform may house one or more liquid medium containers 116. Each liquid medium container 116 may be operably connected to the same collection pad 102, or each liquid medium container 116 may be operably connected to its own collection pad 102. The liquid medium containers 116 may be empty prior to the collection of air by the sampling platform 100. A liquid medium 106 may be poured on top of the collection pad 102, solubilizing the virus collection zone 124 and then is collected by the liquid medium container 116. The liquid medium 106 may flow through the extraction line 154 to the liquid medium container 116.

In other aspects of the present disclosure, the liquid medium container 116 may house the liquid medium 106 for solubilizing the virus collection zone of the collection pad, such as a viral transport medium (VTM). The water-soluble fibers contaminated with the virus will be later solubilized in the liquid medium 106 housed in the liquid medium container 116. The resulting solution is filtered to remove any undissolved water-soluble fibers or other debris, and the final liquid sample is tested for viral loads using RT-PCR, immunoassay, electrochemical or other sensing detection procedures. In some aspects of the present disclosure, the resulting solution may not need to be filtered. For example, 50 mg of the viral collection zone dissolves in 1 mL of the assay buffer and filtration is unnecessary. After the collection pad is immersed in the solvent, the collection pad dissolves. The collection pad may dissolve in less than thirty seconds. The resulting solution may be homogenized using a micromixer.

The viral RNA will be purified from the eluent, reverse-transcribed to cDNA, and subsequently amplified by PCR in a thermal cycler. The oligonucleotide primers and probes for detection of SARS-CoV-2/H1N1 will be selected from regions of the virus nucleocapsid gene. During amplification, the probe anneals to a specific target sequence located between the forward and reverse primers. The 5' nuclease activity of Taq polymerase then degrades the probe, causing the reporter dye to separate from the quencher dye, generating a fluorescent signal during the extension phase of the PCR cycle. With each cycle, additional reporter dye molecules are cleaved from their respective probes, increasing the signal intensity. Fluorescence intensity will be monitored at each PCR cycle by the employed instrument.

Although RT-PCR-based tests are the current gold standards for quantitating SARS-CoV-2/H1N1 loads in a liquid specimen, these assays require specialized instrumentation, relatively expensive reagents, and expert technicians. Isothermal nucleic acid amplification tests are an alternative to conventional PCR methods that do not require expensive instruments or trained personnel to perform the reaction or quantify the results.

Specifically, the RT-LAMP technology allows rapid (within 1 hour) and sensitive detection of RNA in an easily interpretable colorimetric assay that requires only a heat source. Therefore, we will also analyze our samples using the RT-LAMP technique following procedures described recently to establish its compatibility with our sampling approach. Briefly, all LAMP reactions will be performed following New England Biolab's recommended protocol using WarmStart Colorimetric LAMP 2× Master Mix. The 20-μL reactions with 10 μL LAMP master mix, 2 μL of 10× primer mix, 16 μM of Forward Inner Primer and Backward Inner Primer, 4 μM of Loop Forward and Loop Backward primers (25 or 100 nmol scale IDT), 5 μL nuclease-free water and 3 μL samples will be used. LAMP reactions will be incubated at 65° C. using a thermocycler for 30-60 minutes. For both the RT-PCR and RT-LAMP-based assays, the results will be analyzed for statistical significance based on p-values and/or application of t-tests.

The sampling platform will be a significant advance in that regard allowing air-quality monitoring inexpensively and without the need to alter the facility or raise the noise level in it. The sampling platform may consume about 200 mW of electrical power for operation, fit within a human palm and weigh about 100 g, making it readily deployable even in transportation vehicles. The sampling automatically clears away airborne pathogens from its local environment when capturing them on its collection pad. Moreover, the extent of cleansing realized can be expected to correlate directly with the detection sensitivity of the unit as both quantities scale with the amount of captured viral particles.

In one aspect of the present invention, the quantitation of virus samples captured on PVA fibers using the RT-PCR and RT-LAMP techniques can be assessed. The task may assess the analytical performance of the RT-PCR and RT-LAMP techniques in quantitating viral samples containing different amounts of solubilized commercially available PVA fibers. In particular, the method, system and apparatus establish a range of RT-PCR and RT-LAMP methods applied to quantitating SARS-CoV-2 and H1N1 virus samples. Known amounts of inactivated SARS-CoV-2 and H1N1 particles will be sprayed over pads made from PVA fibers purchased from the Amazon online store for this study. A commercial nebulizer such as the one marketed by Fisher Scientific that allows reasonable control over the particle diameter may be used to generate the spray droplets and aerosols. The SARS-CoV-2 and H1N1 samples will be prepared in the Viral Transport Medium (VTM) recommended by Centers for Disease Control and Prevention (CDC), which is compatible with the RT-PCR and RT-LAMP assays.

The sampling platform may also assess the infectivity of the SARS-CoV-2 and H1N1 viral particles captured on the PVA fibers. This study will be performed by spraying a known amount of aerosols containing live SARS-CoV-2 and H1N1 pathogens on the PVA fibers followed by air-drying them for up to 24 hours. The contaminated fibers will be subsequently dissolved in an Agar medium and analyzed following established cell-culture procedures to determine the infectivity of the captured virus. If the captured viral particles are found to be infective even after air-drying for 24 hours, we will explore disinfecting the fibers by exposure to radiation using "germicidal" lamps available commercially.

In one aspect of the present disclosure, a method for quantifying a viral load from various environments is disclosed and shown in FIG. 6. First a sample platform is provided (Step 200). The sampling platform is configured to quantify viral loads in an environment. Next, the collection pad is placed or secured onto the base (Step 202). Air is passed or sucked through the collection pad for extracting viral particles from the environment (Step 204). A vacuum can be actuated to move the air through the collection pad. Air deflectors can direct air towards the collection pad. Prior to passing through the collection pad, air may be filtered to remove debris. The viral collection zone is removed from the collection pad (Step 206) and the viral collection pad is dissolved in the liquid medium (Step 208) resulting in a solution that can be used to determine the quantity of a viral particles by running a PCR test, immunoassay, electrochemical detection or other sensing techniques. The container housing the resulting solution may be removed from the base of the sampling platform.

In one another aspect of the present disclosure another method for quantifying a viral load from various environments is disclosed and shown in FIG. 7. First, a fomite with viral loading is obtained, such as a face mask, piece of clothing or medical equipment, or air filter is obtained (Step 300). Next, the reservoir is loaded with the liquid medium (Step 302). Next, the fomite is secured to the collection pad of the sampling platform (Step 304). Next, the liquid medium is moved from the reservoir through the fomite or collection pad with pressure or a vacuum (Step 306). Next, viral particles are entrained in the liquid medium (Step 308). Next, the liquid medium and viral particles are filtered (Step 310). Lastly, the viral particles and liquid medium are collected in a container (Step 312).

In another aspect of the present disclosure another method for quantitating a viral load, biological reagent load, or a chemical reagent load from various environments is disclosed and shown in FIG. 8. First, a collection pad for quantifying a viral load is provided (Step 400). The collection pad may include water soluble fabric. Next, the collection pad collects a viral load from an environment (Step 402). The viral load may be collected on a viral collection zone of the of collection pad. The viral collection zone may be made out of the water-soluble fabric. Next, the collection pad or a part of the collection pad is dissolved or solubilized in a liquid medium forming a liquid solution (Step 404). The liquid solution contains the viral load captured on the collection pad. Lastly, the viral load is quantitated or a medical diagnostic test is run (Step 406).

The disclosure is not to be limited to the particular aspects described herein. The foregoing description has been presented for purposes of illustration and description. It is not intended to be an exhaustive list or limit any of the disclosure to the precise forms disclosed. It is contemplated that other alternatives or exemplary aspects are considered included in the disclosure. The description is merely examples of embodiments, processes, or methods of the disclosure. It is understood that any other modifications, substitutions, and/or additions may be made, which are within the intended spirit and scope of the disclosure.

What is claimed is:

1. A method for quantifying a viral load from an environmental sample, the method comprising:
providing a sampling platform configured for quantifying viral loads in an environment, the sampling platform comprising a collection pad, a removable container, a housing, an air pump to move air towards the sampling platform and a base, wherein the collection pad is comprised of a viral collection zone comprised of a first material, an impervious zone comprised of a second material, and a support structure connected to the viral collection zone and the impervious zone;
placing the collection pad on the base;

passing air through the collection pad for extracting the viral particles from the environmental sample, wherein the air is directed by at least the air pump;

removing a viral collection zone from the collection pad; and dissolving the viral collection zone in a liquid medium disposed within the container, to form a resulting solution;

quantifying the viral collection zone in the liquid medium.

2. The method of claim 1, further comprising:

removing the container holding the resulting solution from the base of the sampling platform.

3. The method of claim 1, further comprising:

actuating a pump to provide a vacuum for extracting the viral particles from the environmental sample.

4. The method of claim 1, further comprising:

directing air towards the collection pad utilizing at least one air deflector of the sampling platform.

5. The method of claim 1, wherein the collection pad is comprised of water-soluble fabric.

6. The method of claim 5, wherein the second material of the impervious zone is impervious to air and viral loads.

7. The method of claim 1, further comprising:

filtering debris from the environmental sample utilizing a filter of the sampling platform.

8. A platform for sampling viral particles in an environment and on surfaces, the platform comprising:

a removable collection pad configured for quantifying viral loads in an environmental sample, the collection pad comprising at least water soluble fabric, wherein the water soluble fabric is also adapted to precipitate out of water;

a base operably connected to the collection pad, the base comprising a housing;

at least one pump operably configured to move air through the collection pad for extracting viral particles from the environmental sample, the at least one pump disposed within the housing;

a slot for inserting or removing the removable collection pad;

at least one container configured to collect the viral particles; and a liquid medium disposed within the at least one container, the liquid medium configured to dissolve at least a virus collection zone.

9. The platform for sampling viral particles of claim 8, further comprising one or more securement features for mechanically securing the collection pad to the base.

10. The platform for sampling viral particles of claim 8, further comprising at least one air exit hole configured to direct air out of the base.

11. The platform for sampling viral particles of claim 8, wherein the collection pad further comprises the viral collection zone and an impervious zone, wherein the impervious zone is impervious to air.

12. The platform for sampling viral particles of claim 8, further comprising at least one air deflector configured to direct air towards the collection pad.

13. The platform for sampling viral particles of claim 8, wherein the pump is an air pump.

14. The platform for sampling viral particles of claim 8, further comprising a filter secured above a top of the collection pad to prevent debris from attaching to the collection pad.

15. A collection pad for sampling viral particles, the collection pad comprising:

a viral collection zone configured to capture viral particles from an environmental sample, wherein the viral collection zone comprises a first material, wherein the first material is a water-soluble fabric; and an impervious zone surrounding the viral collection zone comprising a second material, wherein the second material is impervious to air and viral particles;

a support structure connected to the viral collection zone and the impervious zone;

wherein the viral collection zone is configured to dissolve in a liquid medium.

16. The collection pad of claim 15, wherein the viral collection zone is comprised of polyvinyl alcohol fibers.

17. The collection pad of claim 15, wherein the impervious zone is comprised of a polyvinyl chloride sheet.

18. The collection pad of claim 15, wherein the support structure, comprises a mesh support structure.

19. The collection pad of claim 15, wherein the viral collection zone is configured to allow air to pass through a plurality of pores.

20. The collection pad of claim 15, wherein the collection pad is configured to be attached to a sampling platform.

* * * * *